United States Patent
Betrouni et al.

(10) Patent No.: US 10,204,206 B2
(45) Date of Patent: Feb. 12, 2019

(54) MODELLING OF THE ACTION OF AN OPTICAL FIBER IN PHOTODYNAMIC THERAPY TREATMENT, AND ASSISTANCE IN THE PLANNING OF SAID TREATMENT

(75) Inventors: Nacim Betrouni, Mons en Baroeul (FR); Stephan Boukris, Paris (FR); Joseph Hardy, Paris (FR)

(73) Assignee: STEBA MAOR SA, Luxembourg (LU)

( * ) Notice: Subject to any disclaimer, the term of this patent is extended or adjusted under 35 U.S.C. 154(b) by 0 days.

(21) Appl. No.: 13/821,330

(22) PCT Filed: Sep. 6, 2011

(86) PCT No.: PCT/EP2011/065409
§ 371 (c)(1),
(2), (4) Date: Jul. 8, 2013

(87) PCT Pub. No.: WO2012/032060
PCT Pub. Date: Mar. 15, 2012

(65) Prior Publication Data
US 2013/0289963 A1    Oct. 31, 2013

(30) Foreign Application Priority Data
Sep. 7, 2010    (EP) .................................... 10305960

(51) Int. Cl.
*G06F 19/12*    (2011.01)
*A61N 5/06*    (2006.01)

(52) U.S. Cl.
CPC .............. *G06F 19/12* (2013.01); *A61N 5/062* (2013.01); *A61N 2005/063* (2013.01); *A61N 2005/0612* (2013.01)

(58) Field of Classification Search
None
See application file for complete search history.

(56) References Cited

FOREIGN PATENT DOCUMENTS

| RU | 2299083 | 5/2007 |
|----|---------|--------|
| WO | 2010089416 | 8/2010 |

OTHER PUBLICATIONS

Fedele, "Fluorescence photon migration by the boundary element method," J Comp Phys, vol. 210, p. 109-132, 2005.*
International Search Report dated Jan. 13, 2012, Application PCT/EP2011/065409.
"Diverse optical characteristic of the prostate and light delivery system: implications for computer modelling of prostatic photodynamic therapy", Jankun, BJU Intl, vol. 95, p. 1237-1244, 2005.
"Treatment planning and dose analysis for interstitial photodynamic therapy of prostate cancer; Treatment planning and analysis for prostate PDT", Davidson, Phys in Med Biol, vol. 54, p. 2293-2313, 2009.
"Treatment planning using tailored and standard cylindrical light diffusers for photodynamic therapy of the prostate; Treatment planning with tailored and standard diffusers" Rendon, Phys in Med Biol, vol. 53, p. 1131-1149, 2008.

* cited by examiner

*Primary Examiner* — G Steven Vanni
(74) *Attorney, Agent, or Firm* — IPSilon USA, LLP

(57) ABSTRACT

A method (200) for planning of a treatment with photodynamic therapy for a patient includes performing a measurement (230) of the volume of the treatment area by volume reconstruction from digital processing of contours inputted directly into a series of digital images of the area being treated, then determining (250) by calculating the number of optical fibers used, their position relative to the brachytherapy grid and their insertion length which optimizes the correspondence of a total theoretical action volume calculated with the measured volume of the treatment area. The total theoretical action volume is calculated based on the position of each fiber, and an elementary theoretical action volume of a fiber corresponding to the volume of a cylinder with predetermined action radius R, and height corresponding to the insertion length of the fiber.

8 Claims, 6 Drawing Sheets

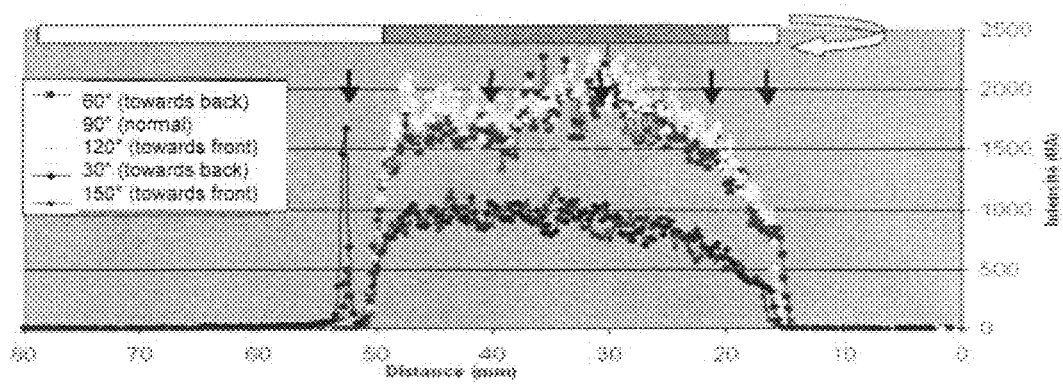
FIG.3
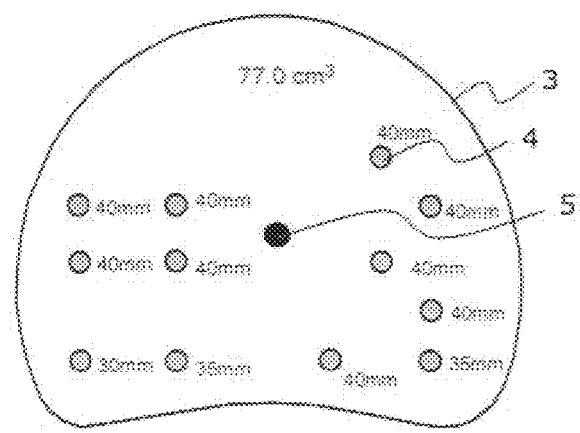
FIG.4
FIG.5
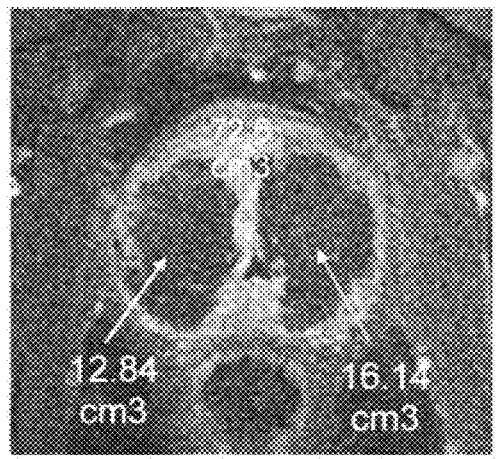

MODELLING OF THE ACTION OF AN OPTICAL FIBER IN PHOTODYNAMIC THERAPY TREATMENT, AND ASSISTANCE IN THE PLANNING OF SAID TREATMENT

RELATED APPLICATIONS

This application is a National Phase Application of PCT/EP2011/065409, filed on Sep. 6, 2011, which in turn claims the benefit of priority from European Patent Application No. 10 305 960.6 filed on Sep. 7, 2010, the entirety of which are incorporated herein by reference.

BACKGROUND

Field of the Invention

This invention concerns a method of modeling the action of an optical fiber for use in treating a patient by photodynamic therapy, and an assistance procedure in the planning of such treatment.

Description of Related Art

Photodynamic therapy, or PDT is a therapy involving administration of a photosensitive substance, which binds preferentially to tissues, e.g. tumor cells, and then irradiates the tissue using a light source with appropriate wavelength, capable of activating the photosensitive substance, which thus releases in situ singlet oxygen or free radicals, which are highly reactive and immediately oxidize adjacent tissue, causing the death of cancer cells by apoptosis (programmed cell death) or by ischemia targeting the blood vessels supplying the tumor cells (Vascular-Targeted Photodynamic Therapy technique or VTP). The oxygen radical species thus produced generally have low coverage and a very short lifetime, so that their toxic effect is very localized. The PDT technique can treat diseases like certain cancers or AMD (Age-Related Macular Degeneration).

Recently, several studies have shown that PDT was an effective alternative for the treatment of prostate cancer by combining the photosensitive substance with specific lasers and dedicated fiber optics.

Thus the Applicant Company has studied various photosensitive agents, especially WST-09, or Tookad®, and more recently WST-11, described in patent applications WO 2004045492 and EP 1137411, which have proven particularly suitable to the treatment of prostate cancer.

In the case of prostate cancer, the photosensitive product is first administered intravenously to the patient in order to be captured by cancer cells. At this stage, the drug remains inactive until it has been exposed to light at the appropriate wavelength.

The light is then applied through a laser supplying several optical fibers positioned under ultrasound guidance. Thus, several optical fibers capable of being powered by a laser are introduced into the prostate. An external grid of the type used in brachytherapy allows the surgeon to precisely position the various optical fibers within the prostate and in relation to each other. More precisely, such a grid includes a plurality of holes arranged in a single plane according to a matrix of several rows and several columns with known spacing. For example, the brachytherapy grid 1 shown in FIG. 1 comprises a matrix of thirteen rows and thirteen columns spaced 0.5 mm apart, with a crossing hole located at each intersection of a row and a column, e.g. hole 2 located at the intersection of column "F" and row "5". Each optical fiber (not shown in FIG. 1) is introduced perpendicular to the external grid through a hole until it enters the area of the prostate to be treated. An ultrasound guide using a probe connected to a control monitor allows the surgeon to visualize the prostate on the screen of the monitor and to introduce each fiber at a given penetration depth.

For effective treatment, the number of fibers used, their positioning in a particular hole of the brachytherapy grid and the length of introduction of each fiber in the treatment area must be precisely determined for each patient. Especially in the case of prostate treatment, individual treatment planning is essential because the different parameters that constitute the number of optical fibers, their position and length of introduction, will clearly vary from one patient to another depending on the nature of the prostate (volume, shape, etc.), the location of cancerous tumors, and therapeutic options (focal treatment, hemiablation, etc.).

Especially from the document "Treatment and planning and dose analysis for interstitial photodynamic therapy of prostate cancer", Sean R H Davidson et al, Phys. Med. Biol. 54 (2009) 2293-2313, a software product is already known for implementing an assistance procedure for planning treatment with photodynamic therapy of the prostate, in order to ensure that a patient will receive a sufficient illumination dose for the target area or treatment area, while minimizing the illumination dose received by surrounding non-target areas. In this document, the plan is based on the prediction of light distribution in the prostate and surrounding areas, and more specifically on solving the equation for the scattering of light by a resolution method with finite elements. Due to the action of the optical fibers associated with the photosensitive substance so modeled, the plan consists of seeking the configuration (especially the number of fibers and positioning of the fibers relative to a brachytherapy grid) for which the light distribution modeled is best appropriate to the treatment of the patient.

The main drawback of this planning method lies in the complex mathematical calculations involved in the modeling. Thus, the total time for obtaining the results of the planning, based on the parameters of the configuration, may exceed several hours. The adjustments made by practitioners (radiologists or surgeons) must be performed iteratively and manually, until obtaining light distribution consistent with that desired.

This method has marked difficulties of application: The introduction of a probe, then optical fibers, within the prostate significantly alters the shape and volume of the prostate, and impacts the coherence of the plan, the model favoring the relative position of optical fibers in relation to the target (treatment area).

Because of the time required for calculation, an adjustment to the parameters actually recorded at the time of treatment (by ultrasound probe) is impractical.

OBJECTS AND SUMMARY

Thus, there is as yet no known method to model the action of optical fibers or assistance in planning for PDT treatment that is simple enough to almost automatically deliver optimized configuration of the parameters to be used in PDT treatment for each patient, and which would require little intervention from the practitioner.

This invention is specifically intended to overcome the drawbacks of known methods by proposing, on the one hand, a modeling tool implemented by computer, based on simple calculations, and on the other hand, a planning tool, also implemented by computer, which is simple to use for the practitioner, and which can deliver very quickly, typically within minutes, a plan tailored to each patient, optimizing for the practitioner the number of fibers used and their lengths and positions (relative to an external grid like that used in brachytherapy).

For this purpose, this invention relates to a modeling method, implemented by computer, of the action of an optical fiber to be used in treatment of a patient by photodynamic therapy to illuminate, at a predefined wavelength, a treatment area on an insertion length of optical fiber within said treatment area, to activate a previously defined photosensitive substance administered to said patient and present in that treatment area, characterized in that it consists of modeling the elementary theoretical action volume of the optical fiber by that of a cylinder with an action radius of R and length L corresponding to said insertion length, and to determine, said action radius R correlating with measured volumes of actual necrotic areas following a plurality of clinical trials conducted on different patients using said photosensitive substance associated with at least one optical fiber, each clinical trial being associated with a set of parameters corresponding to the actual conditions of the clinical trial and including at least the number of optical fibers used, their position relative to a brachytherapy grid, and the insertion length of each fiber in the treatment area, with theoretical action volumes calculated from the same set of parameters and from the elementary theoretical action volume.

The modeling method comprises preferably the following steps:

Construction of a computer database from said clinical trials, by storage for each patient, in said database, of a first digital file corresponding to a series of digital images of the treatment area before the clinical trial, a second digital file corresponding to a series of digital images of the area after the clinical trial, and said set of parameters corresponding to actual conditions of the clinical trial;

Measurement, for each patient in the database, of the volume of the actual necrotic area during the clinical trial, from said first and second digital files;

Calculation, for each patient in the database, of the total theoretical action volume within the parameters of said set and the elementary theoretical action volume of a fiber;

Determination of the action radius R of an optical fiber by correlating the total theoretical action volume calculated for each patient in the database, with the measured volume of the actual necrotic area.

The series of digital images of said first and second digital files correspond preferably to the transverse images of the area before and after treatment, respectively.

The digital images are for instance magnetic resonance or ultrasound images.

In a preferred implementation, the step of measuring the volume of the necrotic area actually includes the following steps:

Loading and displaying of the series of images of the second computer file on a computer graphical user interface displayed on a computer screen;

Contouring of the actual necrotic area by direct input on each image of the series displayed on the computer screen;

Measuring of the volume of the actual necrotic area by volume reconstruction from the digital processing of the contours inputted.

This invention also relates to a method of assistance in the planning of patient treatment by photodynamic therapy using the same principles as those of the above modeling method. More specifically, an assistance method, implemented by computer, for the planning of treatment of a patient by photodynamic therapy, in which a predefined photosensitive material must be administered to the patient, and then subjected to illumination at a predetermined wavelength through a number of optical fibers designed to be introduced over a length of insertion into the treatment area according to a position relative to a brachytherapy grid, is characterized in that it includes the following steps:

Loading and displaying of a digital file corresponding to a series of digital images of the treatment area on a graphical user interface displayed on a computer screen;

Contouring of the treatment area by direct input on each image of the series displayed on the computer screen;

Measuring the volume of the treatment area by volume reconstruction from digital processing of the contours inputted;

Display and Positioning of a flat representation of the brachytherapy grid superimposed on each image of the series and corresponding contours inputted;

determination by calculation of the number of optical fibers used, their positions relative to the brachytherapy grid and their insertion length, which optimizes the correspondence of a total theoretical action volume calculated with the measured volume of the treatment area, said total theoretical action volume being calculated based on the position of each fiber, and an elementary theoretical action volume of a fiber corresponding to the volume of a cylinder with a predetermined action radius R and height corresponding to the insertion length of the fiber.

The action radius R is preferably predetermined according to the modeling method according to the modeling process.

Alternatively, the action radius R is selected from a set of possible values.

In a preferred implementation of the assistance method, the step of determination by calculation uses a gradient descent type optimization algorithm, e.g. the Powell algorithm.

The invention also concerns a computer program product which, when implemented on a computer, performs the modeling method according to invention.

Finally, the invention relates to a computer program product which, when implemented on a computer, performs the planning assistance method according to the invention. Both computer program products can be independent or combined within a single computer program product.

BRIEF DESCRIPTION OF DRAWINGS

The various aspects of the invention will be better understood in light of the following description, made in reference to the accompanying figures in which:

FIG. 3 shows the emission profiles of a particular optical fiber, under different angles of observation, at a wavelength of 763 nm;

FIG. 4 schematically represents an example of a transverse section of a prostate before treatment, and the positioning of optical fibers that were effectively used for PDT treatment in a clinical trial;

FIG. 5 shows an example of a magnetic resonance image showing a transverse section of the prostate, obtained seven days after PDT treatment in a clinical trial;

DETAILED DESCRIPTION

Figure 1:
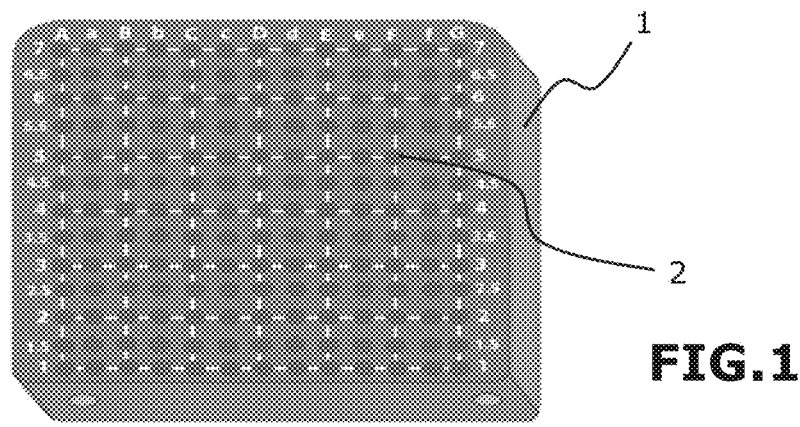
FIG. 1, already described above, is an example of an external brachytherapy type grid, used for positioning a plurality of optical fibers for PDT treatment.

Initially, the various stages of the modeling method, according to the invention, of the action of an optical fiber for use in anti-cancer treatment of a patient by photodynamic therapy, will be detailed with reference to FIG. 2. It is also stressed that this method is intended to be implemented by a software product designed to be installed on a computer. The software product thus includes several routine software, some concerning the stages of calculation or estimation involved in modeling, while others are more specifically related to managing a graphical user interface, capable of being displayed on the screen of the computer, and processing of information that can be inputted by the user via the graphical user interface.

In this study, the Applicant has validated its modeling method for the use of an optical fiber with specific wavelength of 763 nm, in association with the WST11 photosensitive agent, for the treatment of prostate cancer. It is easily understood that the principles of modeling, as well as those of assistance in planning resulting from this modeling, can be used for other combinations of optical fibers and photosensitive agents, and applied to the treatment of other organs.

The modeling method of the invention is essentially based on the fact that the elementary theoretical action volume of the optical fiber considered in combination with the photosensitive agent can be modeled by that of a cylinder with radius R, corresponding to the action radius of the fiber, with length L, corresponding to the length over which the fiber emits light. This model is based on the examination of the emission profiles of the fiber under different viewing angles, shown in FIG. 3. In comparing the various curves corresponding to different viewing angles, one can indeed see that the maximum intensity is obtained for an angle of 90° to the longitudinal axis of the fiber. Accordingly, the Applicant sought a way to determine an action radius R of a fiber based on the results of previous clinical trials.

The Applicant's studies have shown that it was possible to establish an affine relationship, with a correlation coefficient greater than 0.8, between:

firstly, the volume of actual necrotic areas in clinical trials conducted on different patients using the same photosensitive material associated with at least one optical fiber, each clinical trial being associated with a set of parameters corresponding to real clinical trial conditions and including at least the number of optical fibers used, their position relative to a brachytherapy grid, and the insertion length of each fiber in the treatment area, and secondly, the theoretical action volumes calculated from the same set of parameters and the elementary theoretical action volume of a fiber.

Since theoretical action volumes depend on the elementary theoretical action volume of a fiber, which is in turn function, in particular, of the action radius, it is possible to easily determine the action radius.

Figure 2:
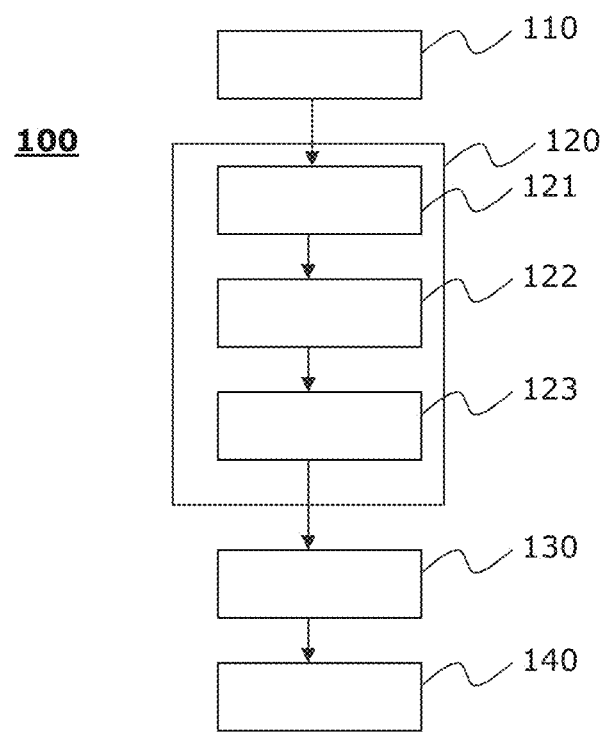
FIG. 2 illustrates, in simplified synoptic form, the steps implemented in a modeling method of the invention.

In reference to FIG. 2, the modeling method 100 thus includes a preliminary step 110 of constructing a database of results from clinical trials conducted previously on a plurality of patients using the same photosensitive material at the same dosage, such as 4 mg/kg of WST11, associated with at least one optical fiber that we seek to model. This construction consists of storing one record per patient in the database with at least the following elements:

a first digital file corresponding to a series of magnetic resonance images of the treatment area before the clinical trial, preferably a series of transverse images;

a second digital file corresponding to a series of magnetic resonance images of the area after the trial, preferably a few days after treatment of the area by PDT;

all parameters corresponding to actual implementation conditions of the clinical trial, including at least the number of optical fibers used, their position on the brachytherapy grid, and the introduction length of each of the fibers in the treatment area.

For example, FIG. 4 schematically represents a transverse section of a prostate with contour 3 before treatment, the optical fibers 4 that were actually used for PDT treatment in the clinical trial in question, namely twelve identical optical fibers and their positioning. The central point 5 schematically represents the position of the urethra. Next to each point representing an optical fiber, a number indicates the insertion length of each fiber into the prostate. FIG. 5 shows the same transverse section of the prostate obtained by magnetic resonance image taken seven days after PDT treatment.

Once the database is created, a step 120 of the procedure is implemented in order to determine, by measuring for each patient in the database, i.e. for each record in the database, the volume of the actual necrotic area in the clinical trial, based on said first and second digital files.

In a preferred embodiment of the invention, this step 120 advantageously includes a first step 121 during which the series of images of the second file is loaded and displayed, frame-by-frame, on a graphical user interface (not shown) displayed on a computer screen. The user, in this case the radiologist or surgeon, can then proceed, in a step 122, to the contouring of the area which was actually necrotic by direct input on each image in the series displayed on the computer screen, preferably via the mouse connected to the computer. The contour submitted by the practitioner is displayed directly superimposed on each image, allowing him to make any contour modifications that become necessary before moving to the next step. The volume of the actual necrotic area can then be effectively calculated in a step 123, by volume reconstruction from a conventional digital processing of contours inputted.

Steps 121-123 are repeated for each record of the database. Following step 120, all the volumes of actual necrotic areas are also provided for all clinical trials stored in the database.

The next step 130 of the method according to the invention, which can actually be conducted either before, after or even simultaneously with step 120, then consists of determining, for each patient in the database, the total theoretical action volume based on the total number of fibers, the position of each fiber, the insertion length of each fiber and the elementary theoretical action volume of an optical fiber, given by the following equation:

$$V=\pi R^2 L$$

Figure 6:
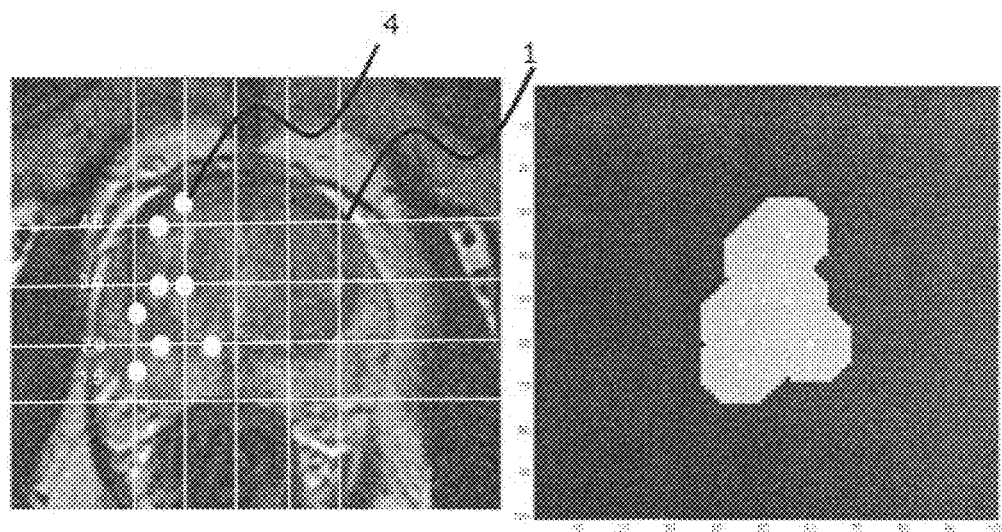
FIG. 6 schematically illustrates the principle of modeling the action of a set of optical fibers according to their relative positions on a brachytherapy grid.

Again, this volume is calculated by conventional methods of volume reconstruction, but taking into account here, in each transverse section plane, the overall contour of the body of optical fibers, each fiber being treated as a cylinder, FIG. 6 shows an example a comparison between a transverse magnetic resonance image of a prostate obtained from the second digital file in which the position of the optical fibers 4 actually used during the corresponding clinical trial appears superimposed, related to the brachytherapy grid 1 (left side of FIG. 6) and the overall contour, at the same level, when the action volume of each fiber, represented by a white rectangle, is modeled by a cylinder (right side of FIG. 6).

Once steps 120 and 130 have been carried out, the only thing left to do is to determine, in a step 140 referenced in FIG. 2, the action radius R of an optical fiber by correlation, for each patient in the database, with the total theoretical action volume calculated with the measured volume of the actual necrotic area.

The modeling method 100 described above has been validated on a database compiled from results from 28 clinical trials performed with a dosage of 4 mg per kilogram of patients involved, each time using a number of fibers with insertion lengths ranging from 15 to 40 mm by increments of 5 mm.

Figure 7:
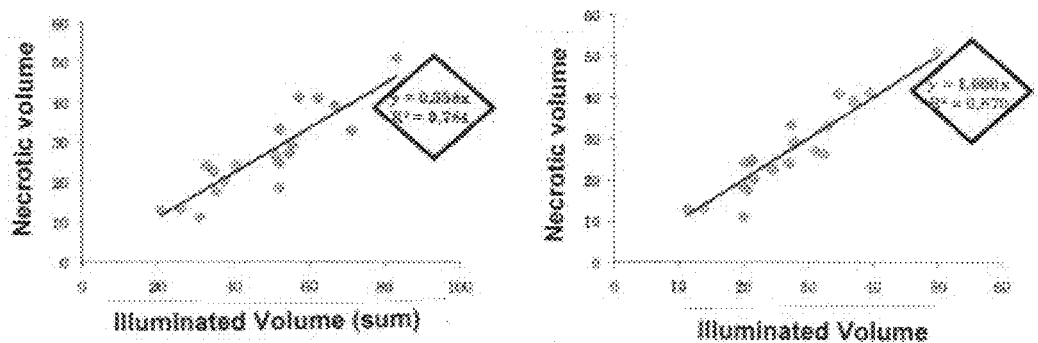
FIG. 7 illustrates the results of various correlations conducted to validate the model.

The curve on the right side of FIG. 7 shows the very good correlation (correlation index equal to 0.87) obtained between the theoretical volumes and volumes of actual necrotic areas resulting from clinical trials. In seeking the value of R for which the theoretical volume was closest to the volume of the actual necrotic area for the 28 clinical trials, an average radius of 7.49 mm with an accuracy of 1.08 mm was found.

Figure 8:
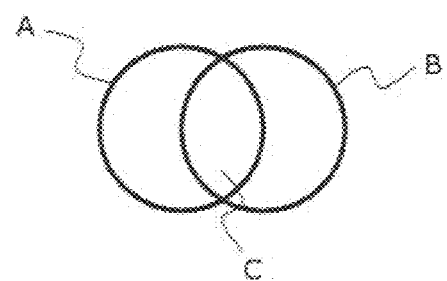
FIG. 8 schematically illustrates two optical fibers positioned to create an overlap area.

The graph on the left side of FIG. 7 in turn represents the results of a correlation of the actual necrotic volume with the sum of elementary volumes of fiber. It is therefore noted that a much better correlation is obtained by considering the actual volume formed by all the fibers according to their position, rather than the sum of the elementary volumes of the fibers, because it can take into account the fact that, when two fibers A and B are positioned so as to have an overlapping area C, as illustrated by the example in FIG. 8, the actual volume does not correspond to the sum of the elementary volumes of the two separate fibers, but to the sum of these elementary volumes less the common volume. In other words, in the modeling, the action of a fiber should not be considered in a part of the volume already covered by the action of another fiber, because the cells in the coverage area may be necrotic only once.

Figure 9:
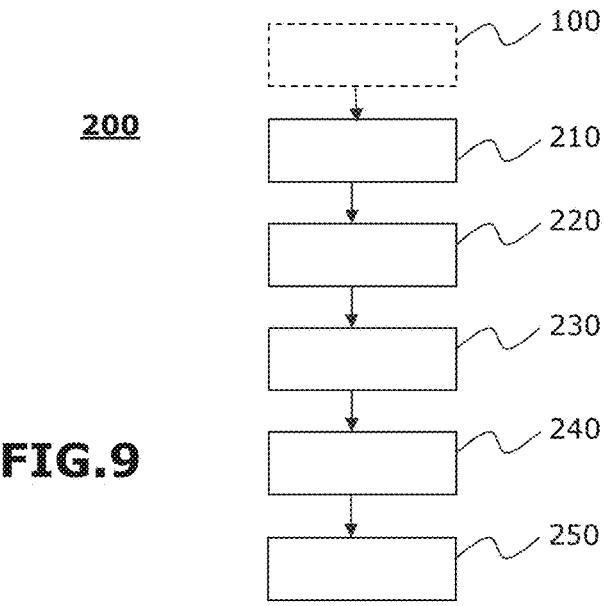
FIG. 9 shows, in simplified synoptic form, different steps implemented in a planning assistance method according to the invention.

The modeling results described above can now be used in planning any future PDT treatment, implementing the method 200 of planning assistance according to the invention which will now be described, particularly in reference to FIG. 9. Again, the assistance method is to be implemented by a software product designed to be installed on a computer, and some process steps require the intervention of the user, typically the practitioner, through a graphical interface designed to be displayed on the computer screen, and controlled by the software product. The objective of this planning is to quickly deliver to the practitioner a set of parameters, optimized in terms of numbers of fibers used, their positioning relative to a brachytherapy grid, and length of insertion into the treatment area, for any patient undergoing photodynamic therapy.

To implement the various steps 210-240 which will now be detailed, calibration of the software product must have previously been carried out to determine the value of the action radius R of an optical fiber. This can be achieved by storing the otherwise determined value of R, or by allowing the user to choose a value of R from a set of possible values, for example the set of values {5.5 mm, 5 6 mm, 6.5 mm, 7.5 mm, 8.5 mm}. Preferably, however, as shown in FIG. 9, the value of R is determined within the same software product, implementing the steps of the modeling method 100 described above. Thus, it is possible to recalibrate the value of the action radius at any time, taking any new clinical trials into account.

Figure 10:
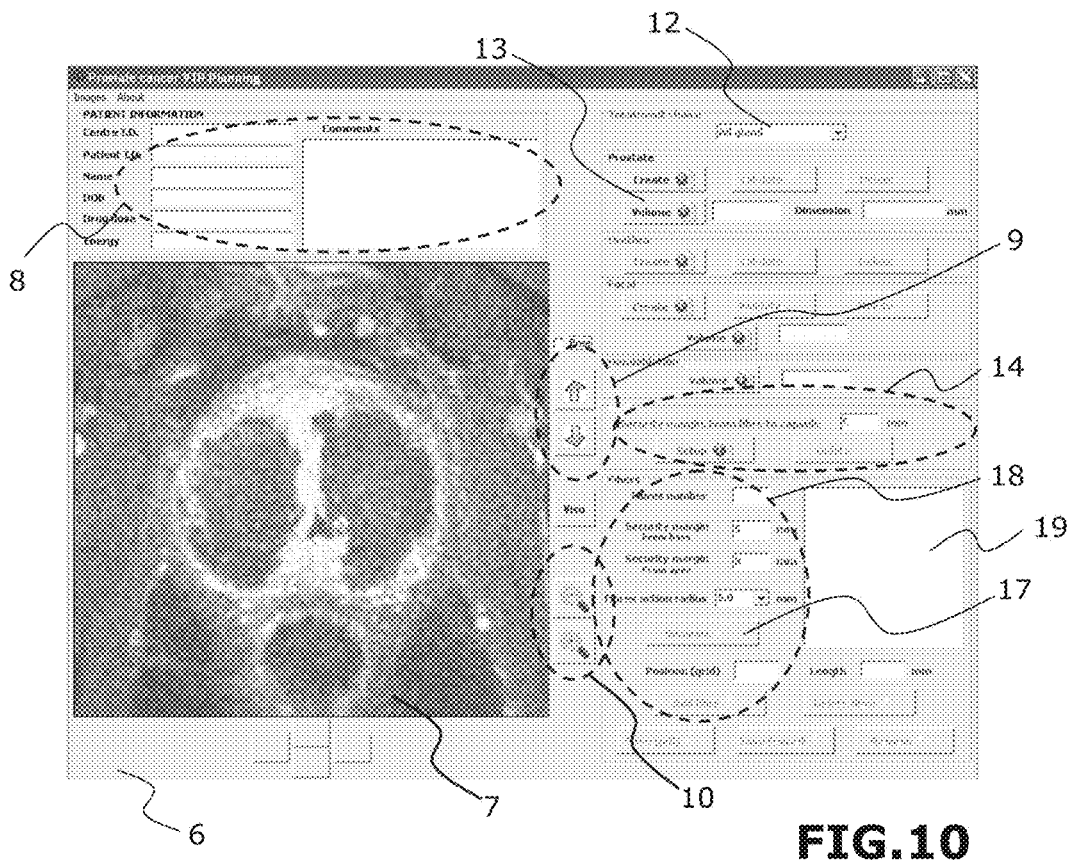
FIG. 10 is a copy of a computer screen representing a graphical user interface after the first stage of the planning assistance method according to the invention.

A first step 210 of the assistance method then consists of enabling the loading and displaying of a digital file corresponding to a series of digital images, either magnetic resonance or ultrasound, preferably flat transverse sections, of the treatment area on a graphical user interface displayed on a computer screen. The digital file is, for example, in DICOM format. FIG. 10 shows, for example, a copy of a computer screen representing the graphical user interface 6 with an area in which a transverse image 7 of a patient's prostate was loaded for display. As you can see from this screenshot, the graphical interface 6 also includes an information zone 8 with several fields that the user can fill out by direct input via a keypad connected to the computer, and various command buttons to allow the user to trigger multiple actions. In particular, after step 210, the user can navigate between different sections of the digital file of images with the navigation buttons of a zone 9 of the interface, to zoom in and respectively zoom out on each image 7 displayed via two buttons on a zone 10 of the interface. Other buttons allow moving the displayed image or changing the contrast. Various patient information can be inputted directly into the interface zone 8, for example the examination center, the patient's identifier and name, his date of birth, the dose and energy delivered, and any appropriate comments. All this information is saved after planning, for example, in a PDF file.

Figure 11:
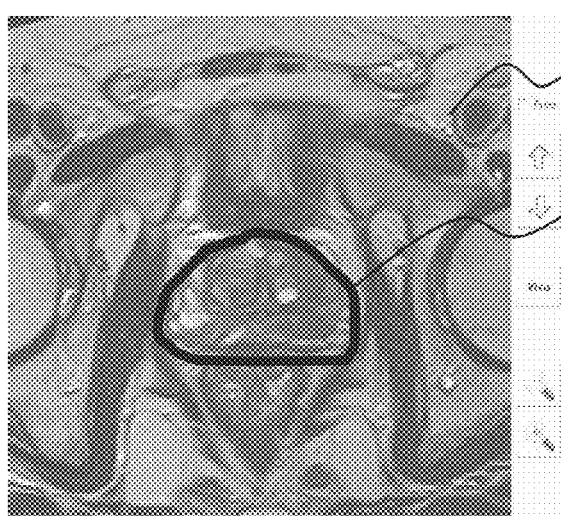
FIGS. 11, 12a and 12b are screenshots representing display examples in a visualization area of the graphical user interface at different stages of the planning assistance method according to the invention.

Following step 210, the practitioner can proceed directly to the graphical interface 6 to a step 220 for contouring the treatment area. This contouring is done by direct input on each image 7 of the series displayed on the graphical interface 6, preferably via the mouse connected to the computer. The contour inputted by the practitioner is displayed directly superimposed on each image, allowing him to make any contour modifications that become necessary before moving to the next step. FIG. 11 shows, as an example, a computer screenshot showing the area of the graphical user interface where a contour 11, drawn by the user, can be displayed, superimposed on the flat transverse image 7.

It should be noted here that, during a PDT treatment of prostate cancer, different areas of the gland may be treated. In accordance with these different clinical procedures, the method of assistance implemented by computer advantageously allows the user to define the appropriate procedure for the patient. It offers four options:

Treatment of the entire gland;
Treatment of the right lobe (right hemiablation);
Treatment of the left lobe (left hemiablation);
Focal treatment.

Prior to the contouring step 220, the user can advantageously choose the type of treatment he envisages, for example through a selection zone 12 by pull-down menu of the graphical user interface (see FIG. 10).

Depending on the type of treatment selected, the user may have to enter, in addition to the contour of the prostate, other contours more precisely defining the treatment area.

After the contouring step 220, one thus has a series of MRI of transverse sections and contours of the treatment area, which appear superimposed on the display of the graphical user interface. The same navigation buttons 9, magnification 10, contrast change or movement as those described above can be used at this point. The contours may advantageously be saved for reloading and viewing at any later time.

The next step 230 of the planning assistance method according to the invention then consists of measuring the volume of the treatment area by volume reconstruction from a conventional digital processing of the contours inputted in step 220. This step is preferably triggered by the user action on a specific command button such as button 13 shown in FIG. 10, if the treatment area is the entire prostate. The volume thus measured is advantageously displayed in cm$^3$ on the graphical interface. When the measured volume is that of the prostate, one can also calculate and display the maximum size of the prostate in millimeters on three spatial planes (transverse, sagittal and coronal).

The step 240 following the planning assistance method according to the invention consists of displaying and positioning a flat representation of the brachytherapy grid superimposed on each image of the corresponding series and contours inputted. For this purpose, the user must select an image from the series of previously loaded transverse images, preferably that corresponding to the central cut of the series. The selected image is displayed in the corresponding display area of the graphical interface, with the superimposed contour(s) previously inputted in Step 220. At this stage, the user can advantageously define an initial safety margin corresponding to the minimum distance required between the positions of eligible fibers and the capsule of the prostate. This distance is by default initialized at a predetermined fixed value, e.g. equal to 6 mm, but can be modified through the graphical interface in an input area 14 (see FIG. 10). Step 240 is preferably triggered by the user, e.g. by activating a specific action button of the graphical user interface located in the input area 14.

Figure 12A:
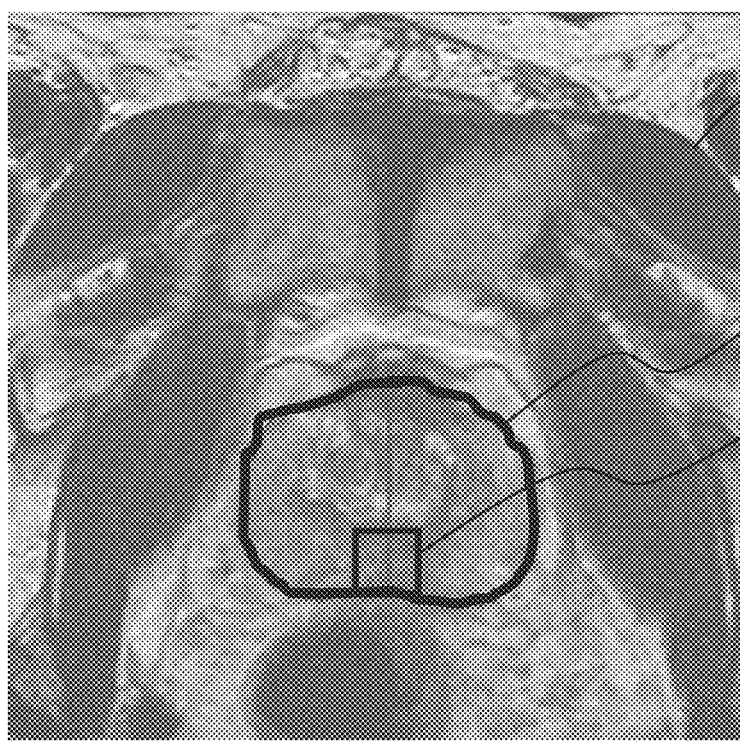
Figure 12B:

FIGS. 12*a* and 12*b* represent, as an example, two screenshots obtained during the implementation of step 240. More specifically, FIG. 12*a* represents the area of the graphical user interface on which the flat transverse image 7 selected appears simultaneously with the previously associated contour 11 inputted by the user (step 220), and a square 15 whose side corresponds to the first safety margin, and whose center corresponds to a specific position on the brachytherapy grid, typically position D1 corresponding to the intersection between the central column D of the grid shown in FIG. 1, and the lower line 1 of this grid. This square can be advantageously moved by the user via the graphical user interface by clicking on its center point.

FIG. 12*b* represents the area of the graphical interface 6 which shows a graphical flat representation 16 of the brachytherapy grid, superimposed over a flat transverse selected image 7 and a corresponding previously inputted contour 11 (step 220). The flat representation 16 appears as a plurality of signs, which here are circles, arranged in a matrix according to the brachytherapy grid in FIG. 1. Colors can be advantageously used at this stage to give a visual indication to the user of the positions of the fibers possibly eligible for treatment. For example, a white circle signifies that the position is not eligible because it is located outside the prostate contour, and a red circle corresponds to a position within the contour of the prostate, but is not eligible either because it is not in the treatment area, or because it is too close to an at-risk area, e.g. capsule or urethra, according to the previously defined margin of safety. A green circle may then mean that a particular position is eligible, thus giving an indication of the maximum number of optical fibers that can be chosen.

The next step 250 (FIG. 9) constitutes the heart of the planning assistance method according to the invention. It concerns the automatic determination by the calculation of optimal parameters in terms of number of optical fibers used, their position on the brachytherapy grid and their length of insertion which will allow obtaining the best match between a total theoretical action volume calculated with the volume at step 230 of the treatment area.

The calculation of the theoretical action volume is based on the same modeling principles as those explained in reference to the modeling method 100 of FIG. 2. Thus, the total theoretical action volume is calculated based on the position of each fiber and the elementary theoretical action volume of a fiber, the latter elementary volume corresponding to the volume of a cylinder with predetermined action radius R, and height corresponding to the insertion length of the fiber.

To enable optimization, step 250 preferably uses a gradient descent type optimization algorithm, like the Powell algorithm. This algorithm performs one-dimensional minimizations along conjugated directions. Two vectors (or directions) $s_1$ and $s_2$ of $\mathbb{R}^n$ are conjugated vis-à-vis a positive definite symmetric matrix A if $S^T_1 As_2=0$. This algorithm requires the definition of an objective function f to minimize. Here, the function f has been defined so that the algorithm best positions the fibers, namely, with optimal coverage of the target area, but with the constraint that there must not be a necrotic region outside the prostate (outside the target). The function used can be defined mathematically by the following equation:

$$f = \sum_{i=1}^{N} w_1 v_i \cap T - w_2 v_i \cap H$$

Where N is a total number of fibers, i is an index representative of a specific fiber, v is a voxel, T the target area and H that remaining outside the target, and $w_1$ and $w_2$ are fixed positive weights.

In other words, Powell's algorithm is used here to find the best parameter values (N number, position of each fiber i, insertion length) that will minimize the difference between the theoretical volume calculated for different parameter values and the measured volume of the treatment area. In practice, the algorithm will start by imposing a first possible value of N, estimated by dividing the target volume measured in step 230 by the elementary theoretical action volume of a fiber, the latter being equal to $\Pi R^2 L$, where R is the predefined action radius of the fiber.

The algorithm then continues by repeatedly searching for all possible positions and insertion lengths of fibers, those that will allow the algorithm to converge toward the minimum value of the function f. Given the model chosen and the simplicity of the calculations implemented by the algorithm, a result can be obtained very quickly, after a period of several minutes. The calculations are especially fast since the algorithm will consider only the actually eligible positions (green circles on the flat representation of the grid displayed in step 240).

The optimization step 250 is preferably triggered by the user, for example by activating a specific action button 17 of the graphical user interface 6 located in an input area 18 (see FIG. 10).

It should be noted that a greater flexibility of use can also be offered, prompting the user, before launching the optimization 250, to select certain parameters, such as the number of fibers to be used, provided that this number is not incompatible with the maximum number of fibers that are eligible in the treatment area. In this case, the number of fibers is directly inputted by the user, preferably in the input area 18 of the graphical interface. Furthermore, the user can himself define, in addition to the first safety margin cited above, two additional safety margins, a first margin corresponding to the minimum distance between the fiber ends and the capsule of the prostate at base level (set by default at 5 mm) and a second safety margin corresponding to the minimum distance between the fiber ends and the capsule of the prostate at the apex (set by default at 3 mm). These different safety margins may be advantageously modified by the user, by direct input, at the level of the specifically dedicated fields in the input area 18 of the graphical interface. Finally, as already mentioned above, the user can select the R value of the action radius in the value set {5.5 mm, 5.6 mm, 6.5 mm, 7.5 mm; 8.5 mm}.

In all cases, at the end of step 250 for optimization, a result giving the minimum number (chosen by the user or automatically optimized), the position and length of each fiber have been provided, the value of all these parameters having been optimized to the particular case of the patient. This result is advantageously displayed on the graphical user interface, for example, in a specific display area 19 (FIG. 10) close to the input area 18.

In addition to these data, it is also possible to provide for displaying the following additional data:
the rate of coverage of the necrosis compared to the simulated target volume.
an index corresponding to the sum of the lengths of the fibers on the target volume.
the sum of the lengths of the fibers.
A graphical representation of the simulated action volume on MRI images in three incidences (axial—coronal and sagittal).

Obviously, the result is also stored, for example in a PDF file, so that the user may consult it at any time, by displaying on the computer or printing on paper a planning report giving an overview including:
any patient information previously inputted in the graphical interface;
the different volumes measured;
the type of treatment chosen;
the safety margins considered in the optimization;
the action radius of the fibers used;
the number of fibers chosen or optimized;
the position and length of the fibers;
the distances between each fiber
the index, the sum of the lengths of the fibers and coverage rates achieved.
the various MRI cross-sections used for planning.

The planning obtained can be advantageously refined, for example by manually modifying the number of fibers. Each addition or deletion of fiber, the rate of coverage, the index and the sum of the lengths of the fibers are recalculated and displayed on the interface. A new planning for the same patient can also be easily introduced by modifying one or more parameters, chosen among:
positioning of the brachytherapy grid
the number of fibers
the safety margins
the action radius of the fibers

The invention claimed is:

1. An assistance method, implemented by computer, that generates a plan to treat a new patient by photodynamic therapy in which a predefined photosensitive substance is administered to the new patient and then subjected to illumination at a predetermined wavelength through a number of identical optical fibers designed to be introduced over a length of insertion into a treatment area according to a position relative to a brachytherapy grid, each of said number of identical optical fibers being of the type emitting light in a direction perpendicular to the longitudinal axis of the optical fiber, said assistance method comprising:

retrieving an estimated action radius R of one optical fiber in combination with said predefined photosensitive substance, wherein said assistance method includes at least one previous determination of said estimated action radius R by conducting a first phase comprising the steps of:

modeling an elementary theoretical action volume of one optical fiber in combination with said predefined photosensitive substance by the volume of a cylinder with said action radius R and length L that corresponds to an insertion length inserted into a trial treatment area;

constructing a database that includes collected data from a plurality of clinical trials on different trial patients using said predefined photosensitive substance associated with at least one optical fiber, each clinical trial being associated with a set of parameters corresponding to the actual conditions of the clinical trial, said set of parameters including at least the number of optical fibers used, their position relative to a brachytherapy grid, and the insertion length of each fiber in the trial treatment area;

storing, for each trial patient of said plurality of clinical trials, in said database, content including a first digital file corresponding to a series of digital images of the treatment area before the clinical trial, a second digital file corresponding to a series of digital images of the trial treatment area after the clinical trial, and said set of parameters corresponding to said actual conditions of the clinical trial;

measuring, for each trial patient in the database, a volume of the actual necrotic area during the clinical trial, from said content in said database of said first and second digital files;

calculating, for each trial patient in the database, a total theoretical action volume based on said set of parameters and the elementary theoretical action volume of each fiber in combination with said predefined photosensitive substance, wherein the total theoretical action volume corresponds to the superposition of each elementary action volume of each fiber used in the corresponding clinical trial in combination with said predefined photosensitive substance, and wherein each elementary action volume is calculated as being the volume of a cylinder with said estimated action radius R and a length corresponding to the insertion length of the corresponding fiber; and determining said estimated action radius R of an optical fiber in combination with said photosensitive substance by correlating said total theoretical action volume calculated for each trial patient in the database, with the measured volume of the actual necrotic area; and performing a second phase for generating a plan in connection with treatment of said new patient, said second phase comprising the steps of:

loading and displaying a digital file corresponding to a series of digital images of the treatment area for said new patient on a graphical user interface displayed on a computer screen;

contouring said treatment area for said new patient by directly inputting said contour on each image of the series of digital images displayed on the computer screen;

measuring a volume of said treatment area for said new patient by volume reconstruction from digital processing of said input contours;

displaying and positioning a flat representation of the brachytherapy grid superimposed on each image, and input contours thereon, of the series;

determining by calculation the optimized parameters, including the number of optical fibers planned to be used, their positions relative to the brachytherapy grid and their insertion length, said optimized parameters corresponding a total theoretical action volume to said measured volume of said treatment area for said new patient, said total theoretical action volume being calculated based on the position of each fiber and an elementary theoretical action volume of a fiber in combination with said photosensitive material, said elementary theoretical action volume corresponding to a volume of a cylinder with said action radius R estimated in said conducted first phase, and height corresponding to the insertion length of the fiber; and displaying the plan including said calculated number of optical fibers, their positions relative to the brachytherapy grid and their insertion lengths to a physician for performing the treatment of said new patient in accordance with said displayed information.

2. The assistance method according to claim 1, wherein the series of digital images of said first and second digital files for each trail patient comprises transverse images of the trial treatment area before and after said clinical trial, respectively.

3. The assistance method according to claim 2, wherein said digital images of the trial treatment area are magnetic resonance or ultrasound images.

4. The assistance method according to claim 1, wherein the steps of measuring, for each trial patient in the database, a volume of the actual necrotic area during the clinical trial from said content in said database of said first and second digital files includes the steps of:

loading and displaying the series of images of the second computer file on a computer graphical user interface displayed on a computer screen;

contouring over the actual necrotic area by directly inputting said contours on each image of the series of digital images displayed on the computer screen; and measuring the volume of the actual necrotic area by volume reconstruction from the digital processing of said volume within said input contours.

5. The assistance method according to claim 1, wherein said series of digital images of said treatment area for said new patient corresponds to transverse images of the treatment area.

6. The assistance method according to claim 1, wherein said digital images of said treatment area for said new patient are magnetic resonance or ultrasound images.

7. The assistance method according to claim 1, wherein said step of determining by calculation uses a gradient descent type optimization algorithm.

8. The assistance method according to claim 7, wherein said step of determining by calculation uses a Powell algorithm.

\* \* \* \* \*